United States Patent [19]
Young

[11] 4,181,811
[45] Jan. 1, 1980

[54] SELECTIVE REACTION OF 1,4-DISUBSTITUTED AROMATIC COMPOUNDS

[75] Inventor: Lewis B. Young, Skillman, N.J.

[73] Assignee: Mobil Oil Corporation, New York, N.Y.

[21] Appl. No.: 969,744

[22] Filed: Dec. 14, 1978

[51] Int. Cl.$^2$ ............................................. C07C 15/08
[52] U.S. Cl. .................................... 585/486; 585/481
[58] Field of Search ................ 260/674 A, 668 A, 672

[56] References Cited
U.S. PATENT DOCUMENTS

| | | | |
|---|---|---|---|
| 3,770,841 | 11/1973 | Meyers, Jr. | 260/674 A |
| 3,856,872 | 12/1974 | Morrison | 260/668 A |
| 3,856,874 | 12/1974 | Hayward | 260/668 A |
| 3,873,632 | 3/1975 | Pollitzer | 260/668 A |
| 3,948,758 | 4/1976 | Bonacci et al. | 260/668 A |
| 4,100,214 | 7/1978 | Dwyer | 260/668 A |
| 4,101,596 | 7/1978 | Mitchell et al. | 260/668 A |

Primary Examiner—George Crasanakis
Attorney, Agent, or Firm—Charles A. Huggett; Ronald J. Cier

[57] ABSTRACT

Isomeric mixtures of non-polar disubstituted aromatic compounds are brought into contact with a shape selective crystalline zeolite catalyst, under cracking or transalkylation conditions, to undergo selective reaction of the 1,4-isomer, thereby leaving the 1,2-isomer and/or 1,3-isomer in excess of equilibrium. The shape selective zeolite catalyst employed herein comprises a crystalline zeolite having a silica to alumina ratio of at least 12 and a constraint index, as herein defined, within the approximate range of 1 to 12.

60 Claims, No Drawings

SELECTIVE REACTION OF 1,4-DISUBSTITUTED AROMATIC COMPOUNDS

BACKGROUND OF THE INVENTION

Field of the Invention

This invention relates to a process for selectively reacting para isomers in isomeric mixtures of dialkylbenzenes utilizing a specified shape selective crystalline zeolite catalyst.

Background of the Invention

The separation of meta or ortho isomers from para disubstituted aromatic compounds is a difficult but necessary step in the production and isolation of ortho and meta compounds. The approach has most frequently been to take advantage of the differences in the boiling points of the various isomers and utilize fractional distillation to make the separation. However, as can be seen from Table I, the differences between the temperatures at which the isomers boil are in reality so very small that in order to achieve efficient separation one must employ very elaborate and expensive distillation columns.

TABLE I

Boiling Points at 760 mm Hg

![structure with R1 and R2 on benzene]

| | | Isomer | | |
|---|---|---|---|---|
| $R_1$ | $R_2$ | ortho | meta | para |
| $CH_3-$ | $CH_3-$ | 144.4° C. | 139.1° C. | 138.4° C. |
| $CH_3-$ | $CH_3CH_2-$ | 165.2° C. | 161.3° C. | 162.0° C. |
| $CH_3-$ | $CH_3\!\!\diagdown\!\!CH\!\!-\!\!\diagup\!\!CH_3$ | 178.3° C. | 175.1° C. | 177.1° C. |
| $CH_3CH_2-$ | $CH_3CH_2-$ | 183.5° C. | 181.0° C. | 183.8° C. |
| $CH_3\!\!\diagdown\!\!CH\!\!-\!\!\diagup\!\!CH_3$ | $CH_3\!\!\diagdown\!\!CH\!\!-\!\!\diagup\!\!CH_3$ | 210.0° C. | 203.2° C. | 210.3° C. |

U.S. Pat. No. 3,029,300 to Schaeffer discloses a selective clathration process for the separation of xylene isomers, but this also involves an elaborate procedure requiring very specialized and expensive equipment.

A catalytic process for the selective production of particular xylene isomers, involving a platinum on alumina catalyst, is disclosed in U.S. Pat. No. 3,078,318 to Berger.

Selective production of para dialkylbenzenes in the presence of specific zeolite catalysts is described in U.S. Pat. Nos. 3,965,209 to Butter et al; 4,001,346 to Chu; 4,086,287 to Kaeding et al and 4,090,981 to Rodewald.

SUMMARY OF THE INVENTION

It has now been discovered that non-polar 1,2-disubstituted and 1,3-disubstituted aromatic compounds may be conveniently, efficiently and economically recovered on an industrial scale by subjecting mixtures of such compounds containing undesirable 1,4-isomers thereof to treatment with a particular type of crystalline zeolite catalyst. The 1,4-disubstituted isomer is selectively reacted (dealkylated) to give products with significantly lower boiling points to permit a conventional, inexpensive separation thereof, leaving the 1,2- and/or 1,3-disubstituted isomer in excess of equilibrium. Following the teachings of this invention, 1,2-disubstituted and/or 1,3-disubstituted aromatics may be selectively produced either as the sole isomers or as the major isomers of the desired non-polar disubstituted aromatic compound in admixture with a minor amount of the 1,4-disubstituted isomer thereof.

The process of the invention involves contacting an isomeric mixture of disubstituted aromatic compounds, under conversion conditions, with a specific type of shape selective crystalline zeolite catalyst, whereupon the 1,4-disubstituted isomer is selectively cracked or transalkylated leaving the product enriched in 1,2- and/or 1,3-disubstituted isomer.

The selective reaction of the 1,4-disubstituted isomer in the presence of the specified catalyst is conducted at a temperature of between about 150° C. and 800° C., and preferably within the approximate range of 250° C. to 550° C. The zeolite catalyst utilized herein is characterized by a silica to alumina ratio of at least about 12 and a constraint index, as hereinafter defined, within the approximate range of 1 to 12.

DESCRIPTION OF SPECIFIC EMBODIMENTS

The disubstituted aromatic compounds of interest in the process of this invention comprise those defined by the formula:

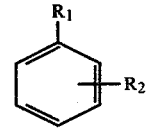

wherein $R_1$ and $R_2$ are both $C_1$ to $C_8$ alkyl, alkylene or alkyne groups and $R_2$ is the same as or different from $R_1$.

In accordance with the present invention, mixtures comprising positional isomers of one or more disubstituted aromatic compounds, said isomers being the 1,2-isomer and/or the 1,3-isomer with at least some of the 1,4-isomer present, are brought into contact, under cracking or transalkylation conditions, with a bed comprising a particulate catalyst containing a crystalline zeolite as hereinafter defined. The 1,4-disubstitutd isomer is selectively dealkylated or transalkylated to facilitate subsequent removal from the mixture, in its entirety or at least in substantial part, by carrying out the process at temperatures of between about 150° C. and 800° C., pressures of between about $10^4$ and about $10^7$ N/m² (about 0.1 to 100 atmospheres), and a feed weight hourly space velocity (WHSV) of between about 0.1 and about 100. The latter WHSV is based upon the weight of the catalyst compositions, i.e. the total weight of active catalyst and binder therefor. It is preferred that contact between the catalyst and the disubstituted aromatic compounds be carried out at from about 250° C. to about 550° C., and at a WHSV of from about 0.2 to 50. Although the reaction normally takes place at atmospheric pressure (i.e. $10^5$ N/m²) the preferred pressure range extends from about $2\times10^4$ to about $2.5\times10^6$ N/m² (0.2 to 25 atmospheres). The 1,2-disubstituted aromatic compounds and/or the 1,3-disubstituted aromatics, singly or together as desired, may subsequently be separated from the reaction effluent by any suitable means.

The process of this invention may be carried out as a batch-type, semi-continuous or continuous operation utilizing a fixed, fluidized or moving bed catalyst system. A preferred embodiment entails use of a fluidized catalyst zone wherein the reactants, i.e. the isomeric mixture of non-polar disubstituted aromatic compounds, are passed concurrently or countercurrently through a moving fluidized bed of the catalyst. The fluidized catalyst after use is conducted to a regeneration zone wherein coke is burned from the catalyst in an oxygen-containing atmosphere, e.g. air, at an elevated temperature, after which the regenerated catalyst is recycled to the conversion zone for further contact with the aromatic reactants.

The process may be carried out in a system wherein the disubstituted compounds are in either the liquid or the vapor state, and the mixture of disubstituted aromatic compounds may be substantially pure (i.e. contain no substantial quantity of hydrocarbon material other than said mixed isomers of said disubstituted aromatic material) or may contain substantial amounts of other hydrocarbon material. The latter situation is such as would exist when the feed stream for the instant process also comprises the effluent stream of an earlier upstream process, for instance a process for the manufacture of disubstituted aromatic compounds. Also, the feed stream for the process of this invention may contain other inert materials as diluents or solvents. Suitable diluents include, but are not limited to: methane, nitrogen, propane, hexane, steam, carbon dioxide, and so forth.

The crystalline zeolites utilized herein are members of a novel class of zeolites that exhibits unusual properties. Although these zeolites have unusually low alumina contents, i.e. high silica to alumina ratios, they are very active even when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by controlled burning at higher than usual temperatures to restore activity. These zeolites, used as catalysts, generally have low coke-forming activity and therefore are conducive to long times on streams between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possesses, in combination: a silica to alumina mole ratio of at least about 12; and a structure providing constrained access to the intracrystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which, due to pore blockage or to other cause, may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of hexane and 3-methylpentane over a small sample, approximately one gram or less, of the zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature adjusted between 290° C. and 510° C. to give an overall conversion between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| Zeolite | C.I. |
| --- | --- |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Beta | 0.6 |
| ZSM-4 | 0.5 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indices. Constraint Index seems to vary somewhat with severity of operation (conversion) and the presence of absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-23, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-23 is more particularly described in U.S. Pat. No. 4,706,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,406,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates for use in this invention are ZSM-5, ZSM-11, ZSM-12, ZSM-23, ZSM-35, and ZSM-38, with ZSM-5, ZSM-11 and ZSM-23 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina ratio of at least about 12 and a dried crystal density of not less than 1.6 grams per cubic centimeter. The dry density for known structures may be calculated from the number of silicon plus aluminum atoms per 1000 cubic Angstroms, as given, e.g. on Page 19 of the article of Zeolite Structure by W. M. Meier. This paper, the entire contents of which are incorporated herein by reference, is included in "Proceedings of the Conference on Molecular Sieves, London, April 1967," published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites including some which are not within the purview of this invention are:

| Zeolite | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | | 1.8 |
| ZSM-23 | | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely, with the zeolite content ranging from between about 1 to 99 percent by weight and more usually in the range of about 5 to about 80 percent by weight of the dry composite.

The crystalline zeolites employed may be modified prior to use by combining therewith a small amount, generally in the range of about 0.5 to about 40 weight percent, preferably of a difficulty reducible oxide, such as the oxides of phosphorous, boron, magnesium or combinations thereof and also oxides of antimony. Modification of the zeolite with the desired oxide or oxides can readily be effected by contacting the zeolite with a solution of an appropriate compound of the element to be introduced, followed by drying and calcining to convert the compound to its oxide form.

Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2O(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the teriary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary; $(RO)_3P$; phosphites; and esters thereof such as the monopropyl ester, alkyl dialkylphosphinites, $(RO)PR_2$, and dialkyl alkylphosphonite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite triethylphosphite, diisopropylphosphite, butylphosphite; and pyrophosphites such as tetraethylpyrophosphite. The alkyl groups in the mentioned compounds contain one to four carbon atoms.

Other suitable phosphorous-containing compounds include the phosphorus halides such as phosphorus trichloride, bromide, and iodide, alkyl phosphorodichloridites, $(RO)PCl_2$, dialkyl phosphorochloridites, $(RO)_2PCl$, dialkylphosphinochloridites, $R_2PCl$, alkyl alkylphosphonochloridates, $(RO)(R)P(O)Cl$, dialkyl phospinochloridates, $R_2P(O)Cl$ and $RP(O)Cl_2$. Applicable corresponding sulfur derivatives include $(RS)PCl_2$, $(RS)_2PX$, $(RS)(R)P(S)Cl$ and $R_2P(S)Cl$.

Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchlorothiophosphate, methyl acid phosphate and other alcohol-$P_2O_5$ reaction products.

Reaction of the zeolite with the phosphorus compound is effected by contacting the zeolite with such compound. Where the treating phosphorus compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as octane may be employed. The phosphorus-containing compound may be used without a solvent, i.e., may be used as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite, such as air or nitrogen, or with an organic solvent, such as octane or toluene.

Prior to reacting the zeolite with the phosphorus-containing compound, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen, for example, air. Heating can be at a temperature of about 150° C. However, higher temperatures, e.g., up to about 500° C., are preferred. Heating is generally carried out for 3–5 hours but may be extended to 24 hours or longer. While heating temperatures above about 500° C. can be employed, they are generally not necessary. At temperatures of about 1000° C. the crystal structure of the zeolite tends to deteriorate.

The amount of phosphorus incorporated with the zeolite should be at least about 0.25 percent by weight. However, it is preferred that the amount of phosphorus in the zeolite be at least about 1 percent by weight when the same is combined with a binder, e.g. 35 weight percent of alumina. The amount of phosphorus can be as high as about 25 percent by weight or more depending on the amount and type of binder present. Preferably, the amount of phosphorus added to the zeolite is between about 0.5 and about 15% percent by weight.

The amount of phosphorus incorporated with the zeolite by reaction with elemental phosphorus or phosphorus-containing compound will depend upon several factors. One of these is the reaction time, i.e., the time that the zeolite and the phosphorus-containing source are maintained in contact with each other. With greater reaction times, all other factors being equal, a greater amount of phosphorus is incorporated with the zeolite. Other factors upon which the amount of phosphorous incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction of the zeolite with the treating compound, and the amount and type of binder incorporated with the zeolite.

Another suitable modifying oxide is that of magnesium. Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium amide, magnesium bromide, magnesium hydride, magnesium lactate, magnesium laurate, magnesium oleate, magnesium palmitate, magnesium salicylate, magnesium stearate and magnesium sulfide.

Reaction of the zeolite with the treating magnesium compound is effected by contacting the zeolite with such compound. Where the treating compound is a liquid, such compound can be in solution in a solvent at the time contact with the zeolite is effected. Any solvent relatively inert with respect to the treating magnesium compound and the zeolite may be employed. Suitable solvents include water and aliphatic, aromatic or alcoholic liquid. The treating compound may also be used without a solvent, i.e. may be used as a neat liquid. Where the treating compound is in the gaseous phase, it can be used by itself or can be used in admixture with a gaseous diluent relatively inert to the treating compound and the zeolite such as helium or nitrogen, or with an organic solvent such as octane or toluene.

Heating of the magnesium compound impregnated catalyst subsequent to preparation and prior to use is preferred. The heating can be carried out in the presence of oxygen, for example, air. Heating can be at a temperature of about 150° C. However, higher temperatures, e.g., up to about 500° C., are preferred. Heating is generally carried out for 1–5 hours but may be extended to 24 hours or longer. While heating temperatures above about 500° C. may be employed, they are generally not necessary. At temperatures of about 1000° C. the crystal structure of the zeolite tends to deteriorate. After heating in air at elevated temperatures, the oxide form of magnesium is present.

The amount of magnesium oxide incorporated in the zeolite should be at least about 0.25 percent by weight. However, it is preferred that the amount of magnesium oxide in the zeolite be at least about 1 percent by weight, particularly when the same is combined with a binder, e.g., 35 weight percent of alumina. The amount of magnesium oxide can be as high as about 25 percent by weight or more depending on the amount and type of binder present. Preferably, the amount of magnesium oxide added to the zeolite is between about 0.5 and about 15 percent by weight.

Boron oxide is also an effective modifying component. Representative boron-containing compounds include boric acid, trimethylborate, boron hydride, boron oxide, boron sulfide, butylboron dimethoxide, butylboronic acid, dimethylboric anhydride, hexamethylborazine, phenylboric acid, triethylborane, tetramethylammonium borohydride, triphenyl boron, and allylborate.

Reaction of the zeolite with the boron compound is effected by contacting the zeolite with such compound. Where the treating boron compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the boron containing compound is, for example, trimethylborate, a hydrocarbon solvent such as octane may be employed. The boron-containing compound may be used without a solvent, i.e. may be used as a neat liquid. Where the boron-containing compound is in the gaseous phase, such as where gaseous diborane is employed, the treating compound can be used by itself or can be used in admixture with a gaseous diluent inert to the boron-containing compound and the zeolite, such as nitrogen or helium, or with an organic solvent, such as octane.

Prior to reacting the zeolite with the boron-containing compound, the zeolite may be dried. Drying can be effected in the presence of air. Elevated temperatures may be employed. However, the temperature should not be such that the crystal structure of the zeolite is destroyed.

Heating of the boron-containing catalyst subsequent to preparation and prior to use is also preferred. The heating can be carried out in the presence of oxygen, for example, air. Heating can be at a temperature of about 150° C. However, higher temperatures, e.g., up to about 500° C., are preferred. Heating is generally carried out for 3-5 hours but may be extended to 24 hours or longer. While heating temperatures above about 500° C. can be employed, they are generally not necessary. At temperatures of about 1000° C. the crystal structure of the zeolite tends to deteriorate.

The amount of boron incorporated with the zeolite should be at least about 0.25 percent by weight. However, it is preferred that the amount of boron in the zeolite be at least about 1 percent by weight when the same is combined with a binder, e.g. 35 weight percent of alumina. The amount of boron can be as high as about 20 percent by weight or more depending on the amount and type of binder present. Preferably, the amount of boron added to the zeolite is between about 1.5 and 10 percent by weight. Without being limited by any theoretical considerations, it is contemplated that boron is actually present in the zeolite in an oxidized state, such as $B_2O_3$.

Antimony oxide may also be employed as a modifying component. The antimony oxide is present as $Sb_2O_3$ alone or in admixture with other antimony oxides with or without metallic antimony or other antimony compounds being present. In all instances, regardless of the particular state of oxidation of the antimony, its content with respect to the zeolite is computed as if it were present as $Sb_2O_3$. Generally the amount of $Sb_2O_3$ in the composite catalyst will be between about 6 and about 40 weight percent and preferably between about 10 and about 35 weight percent. Antimony derivatives which may be used include: the hydride $SbH_3$; the halides $SbX_3$, $SbX_5$ (X=F, Cl, Br, I); organic alkyl and aryl stibines and their oxides $R_3Sb$, $R_5Sb$, $R_xSb=O$ (R=alkyl or aryl); halogen derivatives $RSbX_2$, $R_2SbX$, $RSbX_4$, $R_2SbX_3$, $R_3SbX_2$, $R_4SbX$, the acids $H_3SbO_3$, $HSbO_2$, $HSb(OH)_6$; organic acids such as $RSbO(OH)_2$, $R_2SbO.OH$, all with R and X defined as above noted. Also included are organic ethers such as $R_2SbOSbR_2$; esters and alcoholates such as $Sb(OOCCH_3)_3$, $Sb(OC_4H_9)_3$, $Sb(OC_2H_5)_3$, $Sb(OCH_3)_3$; and antimonyl salts as $(SbO)SO_4$, $(SbO)NO_3$, $K(SbO)C_4H_4O_6$, $NaSbO_2.3H_2O$.

In some instances, it may be desirable to modify the crystalline zeolite by combining therewith two or more of the specified oxides. Thus, the zeolite may be modified by prior combination therewith of oxides of phosphorus and boron, oxides of phosphorus and magnesium or oxides of magnesium and boron. When such modification technique is employed, the oxides may be deposited on the zeolite either sequentially or from a solution containing suitable compounds of the elements, the oxides of which are to be combined with the zeolite. The amounts of oxides present in such instance are in the same range as specified above for the individual oxides, with the overall added oxide content being between 0.5 and about 40 weight percent.

Still another modifying treatment entails steaming of the zeolite by contact with an atmosphere containing from about 5 to about 100 percent steam at a temperature of from about 250° to about 1000° C. for a period of between about 0.25 and about 100 hours and under pressures ranging from sub-atmospheric to several hundred atmospheres to reduce the alpha value thereof to less than 500, and preferably less than 20, but greater than zero.

Another modifying treatment involves precoking of the catalyst to deposit a coating of between about 2 and about 75 and preferably between about 15 and about 75 weight percent of coke thereon. Precoking can be accomplished by contacting the catalyst with a hydrocarbon charge, e.g. toluene, under high severity conditions or alternatively at a reduced hydrogen to hydrocarbon concentration, i.e. 0 to 1 mole ratio of hydrogen to hydrocarbon for a sufficient time to deposit the desired amount of coke thereon.

It is also contemplated that a combination of steaming and precoking of the catalyst under the above conditions may be employed to suitably modify the crystalline zeolite catalyst.

The following examples will serve to illustrate the process of this invention without limiting the concept thereof.

EXAMPLE 1

A diisopropylbenzene (DIPB) mixture containing 68.9 wt.% meta isomer and 23.2 wt.% para isomer was passed over 4.0 grams of HZSM-5 zeolite catalyst in a quartz microreactor at a feed weight hourly space velocity (WHSV) of 4.3 hr.$^{-1}$ and at temperature of 300° C. to 400° C. The results are shown in Table II.

TABLE II

| Selective cracking of diisopropylbenzenes | | | | |
|---|---|---|---|---|
| | Feedstock | | | |
| Catalyst: HZSM-5 | | | | |
| Temperature, °C. | — | 300 | 350 | 400 |
| WHSV, Hr$^{-1}$ | — | 4.3 | 4.3 | 4.3 |
| Composition, wt. % of aromatics | | | | |
| meta-DIPB | 68.9 | 73.0 | 73.0 | 72.0 |
| para-DIPB | 23.2 | 12.5 | 5.9 | 3.1 |
| Benzene | — | 5.2 | 9.4 | 11.7 |
| Toluene | — | 0.4 | 0.8 | 1.4 |
| C$_8$ | — | 0.8 | 1.5 | 2.3 |
| Isopropylbenzene | 0.5 | 2.6 | 1.8 | 1.3 |
| Others | 7.4 | 5.5 | 7.6 | 8.2 |
| % meta in DIPB | 74.8 | 85.4 | 92.5 | 95.9 |

As can be seen, at 400° C. the aromatic effluent from the reactor contained 72.0 wt.% meta-DIPB and 3.1 wt.% para-DIPB. Thus the relative proportion of meta isomer in the DIPB has been increased from 74.8% to 95.9% by selective cracking of the para isomer, yielding benzene as the major cracking product.

EXAMPLES 2 and 3

In separate control experiments, the same DIPB mixture was contacted with low surface area fused quartz chips at 500° C. and WHSV of less than 1 hr$^{-1}$ (Example 2) and with 4.0 grams of a conventional armophous silica-alumina cracking catalyst at 300° C. and 380° C. and WHSV of 4.3 hr$^{-1}$ (Example 3). The results are shown in Table III.

TABLE III

| | Feed. stock | Example 2 | Example 3 | |
|---|---|---|---|---|
| Catalyst | — | Fused Quartz | SiO$_2$ . Al$_2$O$_3$ | |
| Temperature, °C. | — | 500 | 300 | 380 |
| WHSV, Hr$^{-1}$ | — | <1 | 4.3 | 4.3 |
| Composition, wt. % of aromatics | | | | |
| meta - DIPB | 68.9 | 68.2 | 47.2 | 9.9 |

TABLE III-continued

| | Feed stock | Example 2 | Example 3 | |
|---|---|---|---|---|
| para - DIPB | 23.2 | 23.1 | 15.4 | 3.8 |
| Benzene | — | — | 0.6 | 22.4 |
| Toluene | — | — | 0.2 | 1.3 |
| C8 | — | — | 0.7 | 4.5 |
| Isopropylbenzene | 0.5 | 0.6 | 23.3 | 52.5 |
| Others | 7.4 | 8.1 | 12.6 | 5.6 |
| % meta in DIPB | 74.8 | 74.7 | 75.4 | 72.3 |

When the zeolite catalyst was replaced by fused quartz chips (Example 2) essentially no conversion of the DIPB occurred, even at substantially higher temperature and low feed rate thru the reactor then utilized in Example 1. This shows that an acidic catalyst is required for significant conversion of the feedstock. When the identical feedstock was brought in contact with the amorphous $SiO_2.Al_2O_3$ catalyst (Example 3), there was no enhancement of the % meta isomer in the DIPB feed, indicating that no selective cracking of the para isomer had taken place and that a shape selective catalyst is therefore required for selective destruction of the para isomer in preference to the meta isomer.

EXAMPLE 4

The same mixture of meta and para DIPB was contacted with 4.0 grams of another HZSM-5 zeolite catalyst in a flow reactor at both 300° C. and 315° C. and at a WHSV of 4.3 $hr^{-1}$ and 19 $hr^{-1}$, respectively. The results are shown in Table IV.

TABLE IV

| | Feedstock | | |
|---|---|---|---|
| Catalyst: HZSM-5 | | | |
| Temperature, °C. | — | 300 | 315 |
| WHSV, $hr^{-1}$ | — | 4.3 | 19 |
| Composition, wt. % of aromatics | | | |
| meta - DIPB | 68.9 | 61.5 | 67.7 |
| para - DIPB | 23.2 | 8.2 | 12.2 |
| Benzene | — | 13.9 | 9.1 |
| Toluene | — | 1.4 | 1.0 |
| C8 | — | 2.9 | 2.1 |
| Isopropylbenzene | 0.5 | 4.8 | 3.4 |
| Others | 7.4 | 7.3 | 4.5 |
| % meta in DIPB | 74.8 | 88.2 | 84.7 |

Even at relatively high feed rate, it can be seen that the high degree of selectivity of the ZSM-5 catalyst remains substantially unaffected.

EXAMPLE 5

Preparation of Mg-P-ZSM-5 catalyst:
500 grams of $NH_4.ZSM-5$ zeolite catalyst on $Al_2O_3$ was steamed for 1 hour at 543° C., 100% steam and 1 atmosphere of pressure. The steamed catalyst was then treated with a $(NH_4)_2HPO_4$ solution for 16 hours at ambient temperature using 1.66 grams of $H_2O$, 0.568 grams $(NH_4)_2HPO_4$ per gram of catalyst. The treated catalyst was then dried at 120° C. and calcined in air for 3 hours at 500° C. The phosphorus-modified zeolite was then treated with a magnesium acetate solution for 19 hours at ambient temperature using 3 grams magnesium acetate and 4 grams $H_2O$ per gram of catalyst. The treated catalyst was drained of excess solution, dried at 120° C. and calcined in air at 500° C. for 1 hour. The magnesium-phosphorus modified catalyst contained 2.9 wt.% Mg and 3.5 wt.% P.

EXAMPLE 6

A mixture containing 52.0 wt.% meta-ethyltoluene (ET), 47.5 wt.% para-Et and 0.5 wt.% ortho-ET was contacted with 4.0 grams of the Mg-P modified catalyst of Example 5 in a flow microreactor at 400°–500° C. and WHSV of 0.9–6.2 $hr^{-1}$. The results are shown in Table V.

TABLE V

| Selective cracking of ethyltoluene | | | | |
|---|---|---|---|---|
| | Feedstock | | | |
| Catalyst: Mg . P-ZSM-5 | | | | |
| Temperature, °C. | — | 400 | 450 | 500 |
| WHSV, $hr^{-1}$ | — | 0.9 | 2.8 | 6.2 |
| Composition, wt. % of aromatics | | | | |
| Benzene | — | 3.1 | 2.0 | 1.5 |
| Toluene | — | 43.4 | 40.6 | 40.2 |
| Ethylbenzene | — | 3.3 | 1.8 | 0.8 |
| Dimethylbenzenes | — | 5.6 | 3.2 | 2.3 |
| para-Ethyltoluene | 47.5 | 9.3 | 7.3 | 5.2 |
| meta-Ethyltoluene | 52.0 | 32.5 | 43.1 | 49.1 |
| ortho-Ethyltoluene | 0.5 | 1.1 | 1.0 | 0.9 |
| Higher boiling cmpds | — | 1.7 | 1.0 | — |
| % ortho in Ethyltoluene | 0.5 | 2.6 | 2.0 | 1.6 |
| % meta in Ethyltoluene | 52.0 | 75.8 | 83.9 | 89.0 |

It is shown that the level of meta isomer in ethyltoluene, at 500° C. and WHSV of 6.2 $hr^{-1}$, was increased from 52% in the original feed to 89% in the reactor effluent by selective cracking of the para isomer.

EXAMPLE 7

A mixture of 26.0 wt.% meta-, 25.7 wt.% para- and 0.3 wt.% ortho-ethyltoluene in toluene was fed to a quartz microreactor using the same catalyst as Example 5. Conditions and results are shown in Table VI.

TABLE IV

| Selective cracking of ethyltoluene in toluene | | | | |
|---|---|---|---|---|
| | Feedstock | | | |
| Catalyst: Mg . P-ZSM-5 | | | | |
| Temperature, °C. | — | 500 | 550 | 600 |
| WHSV, $hr^{-1}$ | — | 6.2 | 6.2 | 12.4 |
| Composition, wt. % of aromatics | | | | |
| Penzene | — | 1.2 | 2.5 | 2.7 |
| Toluene | 48.0 | 65.6 | 67.1 | 65.8 |
| Ethylbenzene | — | 0.6 | 0.5 | 0.3 |
| Dimethylbenzenes | — | 2.0 | 3.5 | 3.5 |
| para-Ethyltoluene | 25.7 | 5.3 | 2.7 | 1.9 |
| meta-Ethyltoluene | 26.0 | 24.9 | 23.2 | 23.8 |
| ortho-Ethyltoluene | 0.3 | 0.4 | 0.5 | 0.5 |
| Higher boiling cmpds | — | — | — | 1.5 |
| % ortho in Ethyltoluene | 0.6 | 1.3 | 1.9 | 1.9 |
| % meta in Ethyltoluene | 50.0 | 81.4 | 87.9 | 90.8 |

At 500° C. an increase was observed in the level of meta isomer from 50% in the feed to 81.4% in the reactor effluent. Similarly, the meta content increased to 87.9% at 550° C. and 90.8% at 600° C. These results demonstrate that dilution of the reactants with a solvent does not hinder the selective cracking of the para isomer.

EXAMPLE 8

A feedstock containing 24.05 wt.% para-diethylbenzene (DEB) and 25.3 wt.% meta-DEB with 50.4 wt.% benzene was passed over 4.0 grams of the catalyst of Example 5 at 600° C. and WHSV of 12.4 $hr^{-1}$. The products are shown in Table VII.

| Selective cracking in diethylbenzenes | | |
|---|---|---|
| | Feedstock | |
| Catalyst: Mg . P-ZSM-5 | | |
| Temperature, °C. | — | 600 |
| WHSV, hr$^{-1}$ | — | 12.4 |
| Composition, wt. % of aromatics | | |
| Benzene | 50.4 | 61.0 |
| Toluene | — | 1.0 |
| Ethylbenzene | — | 10.0 |
| Dimethylbenzenes | — | 0.4 |
| para-Ethyltoluene | 0.3 | 1.4 |
| meta-Ethyltoluene | — | 0.5 |
| para-Diethylbenzene | 24.05 | 1.1 |
| meta-Diethylbenzene | 25.3 | 24.1 |
| ortho-Diethylbenzene | — | 0.6 |
| Higher boiling cmpds | — | — |
| % meta in Diethylbenzene | 51.3 | 93.4 |

Selective transformation of para-DEB has occurred, with the resultant production of benzene and ethylbenzene. The meta-DEB is largely unreacted. The proportion of the meta isomer in the DEB has increased from 51.3% in the feedstock to 93.4% in the product.

EXAMPLE 9

A feedstock containing 49.5 wt.% meta-t-butyltoluene (t-BT) and 49.1 wt.% para-t-BT was contacted with 4.0 grams of HZSM-5 catalyst in a flow reactor at 420° C. and WHSV of 4.4 hr$^{-1}$. The products are shown in Table VIII.

TABLE VIII

| Selective cracking of t-butyltoluenes | | | |
|---|---|---|---|
| | Feedstock | | |
| Catalyst: HZSM-5 | | | |
| Temperature, °C. | — | 420 | 420 |
| WHSV, hr$^{-1}$ | — | 4.4 | 19.4 |
| Composition, wt. % of aromatics | | | |
| Benzene | — | 2.0 | — |
| Toluene | 0.4 | 59.5 | 26.1 |
| C$_{8,9,10}$ | — | 9.0 | 1.4 |
| para-t-Butyltoluene | 49.1 | 5.2 | 27.4 |
| meta-t-Butyltoluene | 49.5 | 24.2 | 44.7 |
| Higher boiling compounds | 0.9 | 0.1 | 0.4 |
| % meta in t-Butyltoluene | 50.2 | 82.3 | 62.0 |

In both runs the meta isomer has been enriched relative to the para isomer, with the major conversion product being toluene.

EXAMPLE 10

A mixture comprising 63.34 wt.% 1-isopropyl-3-methylbenzene (meta-cymene), 30.32 wt.% 1-isopropyl-4-methylbenzene (para-cymene), and 2.07 wt.% 1-isopropyl-2-methylbenzene (ortho-cymene) was passed through a catalyst bed of 4 grams of HZSM-5 catalyst which had been steamed at 600° C. for one hour with atmospheric steam. The temperature of the bed ranged between 300° C. and 450° C. The results are shown in Table IX.

TABLE IX

| Selective cracking of cymenes | | | |
|---|---|---|---|
| | Feedstock | | |
| Catalyst: HZSM-5 | | | |
| Temperature, °C. | — | 340 | 445 |
| WHSV, hr$^{-1}$ | — | 4.1 | 8.7 |
| Composition wt. % | | | |

TABLE IX-continued

| Selective cracking of cymenes | | | |
|---|---|---|---|
| | Feedstock | | |
| Toluene | — | 20.45 | 22.96 |
| ortho-Cymene | 2.07 | 1.93 | 2.20 |
| meta-Cymene | 63.34 | 61.78 | 61.92 |
| para-Cymene | 30.32 | 0.0 | 0.0 |
| Aromatic C$_{10}$ | 2.15 | 5.13 | 3.16 |
| Other aromatics | 1.39 | 1.15 | 0.05 |
| C$_2$H$_4$ | — | 0.23 | 0.66 |
| C$_3$H$_6$ | — | 2.24 | 5.05 |
| C$_4$H$_8$ | — | 2.28 | 2.10 |
| Other light gases | 1.0 | 4.66 | 1.58 |
| % ortho in Cymene | 2.2 | 3.0 | 3.4 |
| % meta in Cymene | 66.2 | 97.0 | 96.6 |

As can be seen, the para isomer was completely removed by catalytic cracking to lower boiling products, primarily toluene, propylene and butenes. However, the ortho- and-meta-isomers have remained practically unchanged.

EXAMPLE 11

A mixture comprising 66.2 wt.% 1-isopropyl-3-methylbenzene (meta-cymene), 29.8 wt.% 1-isopropyl-4-methylbenzene (para-cymene), and 4.0 wt.% 1-isopropyl-2-methylbenzene (ortho-cymene) was contacted with 4 grams of HZSM-11 zeolite catalyst which had been steamed at 600° C. for 3 hours at atmospheric pressure. The results are summarized in Table X.

TABLE X

| Selective cracking of cymenes | | |
|---|---|---|
| | Feedstock | |
| Catalyst: HZSM-5 | | |
| Temperature, °C. | — | 310 |
| WHSV, hr$^{-1}$ | — | 4.3 |
| Composition, wt. % | | |
| Toluene | — | 36.90 |
| ortho-Cymene | 4.0 | 4.53 |
| meta-Cymene | 66.2 | 39.27 |
| para-Cymene | 29.8 | 1.62 |
| Aromatic C$_{10}$ | — | 3.51 |
| Other aromatics | — | 5.07 |
| C$_2$H$_4$ | — | 0.93 |
| C$_3$H$_6$ | — | 1.68 |
| C$_4$H$_8$ | — | 4.46 |
| Other light gases | — | 2.28 |
| % ortho in Cymene | 4.0 | 10.0 |
| % meta in Cymene | 66.2 | 86.5 |

It is again seen from the above results that the para-isomer has been selectively reduced with corresponding enrichment of both the ortho and meta-isomers in the cymene product fraction.

EXAMPLE 12

Using a process similar to that described in Example 5, a Mg-P modified-ZSM-5 zeolite catalyst was prepared from HZSM-5 having 35% Al$_2$O$_3$ as a binder. The Mg.P-ZSM-5 contained 4.9 wt.% Mg and 3.4 wt.% P.

EXAMPLE 13

A feedstock containing 47.66 wt.% para-ethyltoluene, 0.27 wt.% meta-ethyltoluene and 52.01 wt.% ortho-ethyltoluene was passed over 1.0 gram of the Mg.P modified ZSM-5 catalyst of Example 12 at 400°–500° C. and WHSV of 3.8 hr.$^{-1}$. The results are summarized in Table XI.

TABLE XI

Selective cracking of ethyltoluenes

| | Feedstock | | |
|---|---|---|---|
| Catalyst: Mg . P-ZSM-5 | | | |
| Temperature, °C. | — | 400 | 500 |
| WHSV, hr$^{-1}$ | | 3.8 | 3.8 |
| Composition, wt. % of aromatics | | | |
| Benzene | — | — | 0.61 |
| Toluene | — | 20.44 | 30.68 |
| Aromatic C$_8$ | — | 1.26 | 1.63 |
| ortho-Ethyltoluene | 52.01 | 54.19 | 1.38 |
| meta-Ethyltoluene | 0.27 | 3.05 | 1.38 |
| para-Ethyltoluene | 47.66 | 20.68 | 8.24 |
| Other C$_9$+ Aromatics | — | 0.38 | 0.65 |
| % ortho in Ethyltoluene | 52.0 | 69.6 | 85.5 |
| % meta in Ethyltoluene | 0.3 | 3.9 | 2.1 |

Selective dealkylation of the para-isomer in a mixture of ortho- and para-ethyltoluene has occurred, leaving the product stream significantly enriched in the ortho-isomer.

EXAMPLE 14

A feedstock comprising 68.13 wt.% 1-isopropyl-3-methylbenzene (meta-cymene), 27.54 wt.% 1-isopropyl-4-methylbenzene (para-cymene), and 4.25 wt.% 1-isopropyl-2-methylbenzene (ortho-cymene) was passed through a catalyst bed of 1.0 gram of an HZSM-23 zeolite catalyst in a flow reactor at 300°–400° C. and a WHSV of 3.8 hr$^{-1}$. The runs are summarized in TABLE XII below.

TABLE XII

Selective cracking of Cymenes

| | Feedstock | | | |
|---|---|---|---|---|
| Catalyst: HZSM-23 | | | | |
| Temperature, °C. | — | 300 | 350 | 400 |
| WHSV, hr$^{-1}$ | — | 3.8 | 3.8 | 3.8 |
| Composition, wt. % of aromatics | | | | |
| Toluene | — | 14.2 | 30.7 | 45.5 |
| Dimethylbenzenes | — | — | — | 1.1 |
| ortho-Cymene | 4.25 | 4.2 | 2.9 | 1.7 |
| meta-Cymene | 68.13 | 64.4 | 55.3 | 38.9 |
| para-Cymene | 27.54 | 11.5 | 2.8 | 1.8 |
| n-Propyltoluene | — | — | — | 0.9 |
| % ortho in Cymenes | 4.3 | 5.2 | 4.8 | 4.0 |
| % meta in Cymenes | 68.1 | 80.4 | 90.7 | 91.8 |

As will be apparent from the data, the HZSM-23 zeolite catalyst has selectively dealkylated the para-isomer, leaving the product stream signficantly enriched in meta-cymene at all temperatures.

Having thus generally described the process of the present invention and set forth specific examples in support thereof, it is to be understood that no undue restrictions are to be imposed on the scope of the concept disclosed herein by reason of the illustrative examples.

What is claimed is:

1. A process for selective reaction of 1,4-disubstituted aromatic compounds in a mixture comprising disubstituted aromatic isomers, the process comprising contacting said mixture, under conversion conditions, with a crystalline zeolite catalyst, said catalyst characterized by a silica to alumina ratio of at least about 12 and a constraint index within the approximate range of 1 to 12, to yield a product in which the content of said 1,4-disubstituted aromatic compounds is reduced relative to the content of said disubstituted aromatic isomers in said mixture prior to said contacting.

2. The process of claim 1 wherein said 1,4-disubstituted aromatic compound is a 1,4-dialkylbenzene.

3. The process of claim 2 wherein said 1,4-dialkylbenzene is 1,4-diisopropylbenzene.

4. The process of claim 2 wherein said 1,4-dialkylbenzene is 1-ethyl-4-methylbenzene.

5. The process of claim 2 wherein said 1,4-dialkylbenzene is 1,4-diethylbenzene.

6. The process of claim 2 wherein said 1,4-dialkylbenzene is 1-t-butyl-4-methylbenzene.

7. The process of claim 2 wherein said 1,4-dialkylbenzene is 1-isopropyl-4-methylbenzene.

8. The process of claim 1 wherein said conversion conditions include a temperature between about 150° C. and about 800° C., a pressure between about $10^4$ N/m$^2$ and about $10^7$ N/m$^2$.

9. The process of claim 1 wherein said conversion conditions include a temperature between about 250° C. and about 550° C., a pressure between about $2 \times 10^4$ N/m$^2$ and about $2.5 \times 10^6$ N/m$^2$.

10. The process of claim 1 wherein said crystalline zeolite has undergone prior modification by combining therewith between about 0.5 and about 40 weight percent of at least one oxide selected from the group consisting of the oxides of phosphorus, antimony, boron and magnesium.

11. The process of claim 1 wherein said crystalline zeolite has undergone prior modification by combining therewith between about 1 and about 25 weight percent of an oxide of phosphorus.

12. The process of claim 1 wherein said crystalline zeolite has undergone prior modification by combining therewith between about 1 and about 25 weight percent of an oxide of magnesium.

13. The process of claim 1 wherein said crystalline zeolite has undergone prior modification by steaming at a temperature between about 250° C. and about 1000° C. for a period of between about 0.5 and about 100 hours.

14. The process of claim 1 wherein said crystalline zeolite is ZSM-5.

15. The process of claim 14 wherein said ZSM-5 is admixed with a binder therefor.

16. The process of claim 1 wherein said crystalline zeolite is ZSM-11.

17. The process of claim 16 wherein said ZSM-11 is admixed with a binder therefor.

18. The process of claim 1 wherein said crystalline zeolite is ZSM-23.

19. The process of claim 18 wherein said ZSM-23 is admixed with a binder therefor.

20. The process of claim 1 wherein said mixture containing said 1,4-disubstituted aromatic compound is admixed with a diluent prior to contacting it with said zeolite catalyst.

21. A process for the manufacture of 1,3-disubstituted aromatic compounds by the selective reaction of the 1,4-disubstituted isomer thereof from mixtures comprising both isomers, either alone or in admixture with other aromatic or non-aromatic materials, said process comprising contacting said mixture, under conversion conditions, with a crystalline zeolite catalyst, said catalyst characterized by a silica to alumina ratio of at least about 12 and a constraint index within the approximate range of 1 to 12, to yield a resulting product in which the ratio of the 1,3-isomer to the 1,4-isomer of said disubstituted aromatic compound is increased relative to the ratio of said isomers in said mixture prior to contacting it with said zeolite catalyst.

22. The process of claim 21 wherein said disubstituted aromatic compound is a dialkylbenzene.

23. The process of claim 22 wherein said dialkylbenzene is diisopropylbenzene.

24. The process of claim 22 wherein said dialkylbenzene is ethylmethylbenzene.

25. The process of claim 22 wherein said dialkylbenzene is diethylbenzene.

26. The process of claim 22 wherein said dialkylbenzene is t-butylmethylbenzene.

27. The process of claim 22 wherein said dialkylbenzene is isopropylmethylbenzene.

28. The process of claim 21 wherein said conversion conditions include a temperature between about 150° C. and about 800° C., a pressure between about $10^4$ N/m$^2$ and about $10^7$ N/m$^2$.

29. The process of claim 21 wherein said conversion conditions include a temperature between about 250° C. and about 550° C., a pressure between about $2 \times 10^4$ N/m$^2$ and about $2.5 \times 10^6$ N/m$^2$.

30. The process of claim 21 wherein said crystalline zeolite has undergone prior modification by combining therewith between about 0.5 and about 40 weight percent of at least one oxide selected from the group consisting of the oxides of phosphorus, antimony, boron and magnesium.

31. The process of claim 21 wherein said crystalline zeolite has undergone prior modification by combining therewith between about 1 and about 25 weight percent of an oxide of phosphorus.

32. The process of claim 21 wherein said crystalline zeolite has undergone prior modification by combining therewith between about 1 and about 25 weight percent of an oxide of magnesium.

33. The process of claim 21 wherein said crystalline zeolite has undergone prior modification by steaming at a temperature between about 250° C. and about 1000° C. for a period of between about 0.5 and about 100 hours.

34. The process of claim 21 wherein said crystalline zeolite is ZSM-5.

35. The process of claim 34 wherein said ZSM-5 is admixed with a binder therefor.

36. The process of claim 21 wherein said crystalline zeolite is ZSM-11.

37. The process of claim 36 wherein said ZSM-11 is admixed with a binder therefor.

38. The process of claim 21 wherein said crystalline zeolite is ZSM-23.

39. The process of claim 38 wherein said ZSM-23 is admixed with a binder therefor.

40. The process of claim 21 wherein said mixture containing said disubstituted aromatic compounds is admixed with a diluent prior to contacting it with said zeolite catalyst.

41. A process for the manufacture of 1,2-disubstituted aromatic compounds by the selective reaction of the 1,4-disubstituted isomer thereof from mixtures comprising both isomers, either alone or in admixture with other aromatic or non-aromatic materials, said process comprising contacting said mixture, under conversion conditions, with a crystalline zeolite catalyst, said catalyst characterized by a silica to alumina ratio of at least about 12 and a constraint index within the approximate range of 1 to 12, to yield a resulting product in which the ratio of the 1,2-isomer to the 1,4-isomer of said disubstituted aromatic compound is increased relative to the ratio of said isomers in said mixture prior to contacting it with said zeolite catalyst.

42. The process of claim 41 wherein said disubstituted aromatic compound is a dialkylbenzene.

43. The process of claim 42 wherein said dialkylbenzene is diisopropylbenzene.

44. The process of claim 42 wherein said dialkylbenzene is ethylmethylbenzene.

45. The process of claim 42 wherein said dialkylbenzene is diethylbenzene.

46. The process of claim 42 wherein said dialkylbenzene is t-butylmethylbenzene.

47. The process of claim 42 wherein said dialkylbenzene is isopropylmethylbenzene.

48. The process of claim 41 wherein said conversion conditions include a temperature between about 150° C. and about 800° C., a pressure between about $10^4$ N/m$^2$ and about $10^7$ N/m$^2$.

49. The process of claim 41 wherein said conversion conditions include a temperature between about 250° C. and about 550° C., a pressure between about $2 \times 10^4$ N/m$^2$ and about $2.5 \times 10^6$ N/m$^2$.

50. The process of claim 41 wherein said crystalline zeolite has undergone prior modification by combining therewith between about 0.5 and about 40 weight percent of at least one oxide selected from the group consisting of the oxides of phosphorus, antimony, boron and magnesium.

51. The process of claim 41 wherein said crystalline zeolite has undergone prior modification by combining therewith between about 1 and about 25 weight percent of an oxide of phosphorus.

52. The process of claim 41 wherein said crystalline zeolite has undergone prior modification by combining therewith between about 1 and about 25 weight percent of an oxide of magnesium.

53. The process of claim 41 wherein said crystalline zeolite has undergone prior modification by steaming at a temperature between about 250° C. and about 1000° C. for a period of between about 0.5 and about 100 hours.

54. The process of claim 41 wherein said crystalline zeolite is ZSM-5.

55. The process of claim 54 wherein said ZSM-5 is admixed with a binder therefor.

56. The process of claim 41 wherein said crystalline zeolite is ZSM-11.

57. The process of claim 56 wherein said ZSM-11 is admixed with a binder therefor.

58. The process of claim 41 wherein said crystalline zeolite is ZSM-23.

59. The process of claim 58 wherein said ZSM-23 is admixed with a binder therefor.

60. The process of claim 41 wherein said mixture containing said disubstituted aromatic compounds is admixed with a diluent prior to contacting it with said zeolite catalyst.

* * * * *

UNITED STATES PATENT AND TRADEMARK OFFICE
CERTIFICATE OF CORRECTION

PATENT NO. : 4,181,811
DATED : January 1, 1980
INVENTOR(S) : Lewis Brewster Young It is certified that error appears in the above-identified patent and that said Letters Patent are hereby corrected as shown below:

| | |
|---|---|
| Column 5, line 23 | "presence of" should be -- presence or -- |
| Column 5, line 59 | "4,706,842" should be -- 4,076,842 -- |
| Column 5, line 65 | "4,406,859" should be -- 4,046,859 -- |
| Column 6, line 43 | "article of" should be -- article on -- |
| Column 8, line 1 | "difficulty" should be -- difficultly -- |
| Column 8, line 13 | "$R_2O(S)SX$" should be -- $R_2P(S)SX$ -- |
| Column 8, line 19 | "teriary" should be -- tertiary -- |
| Column 8, line 36 | "trimethylphosphite" should be followed by --,-- |
| Column 13, line 15 | "then" should be -- than -- |
| Column 14, line 37 | "TABLE IV" should be -- TABLE VI -- |
| Column 14, line 45 | "Penzene" should be -- Benzene -- |
| Column 15, line 1 | -- TABLE VII -- should be inserted |
| Column 16, line 34 | "HZSM-5" should be -- HZSM-11 -- |
| Column 17, line 12 | "1.38" should be -- 56.82 -- |

Signed and Sealed this

Tenth Day of June 1980

[SEAL]

Attest:

SIDNEY A. DIAMOND

Attesting Officer

Commissioner of Patents and Trademark